United States Patent [19]
Piantadosi et al.

[11] Patent Number: 5,512,671
[45] Date of Patent: Apr. 30, 1996

[54] ETHER LIPID-NUCLEOSIDE COVALENT CONJUGATES

[75] Inventors: Claude Piantadosi, Chapel Hill, N.C.; Canio J. Marasco, Jr., Tonawanda, N.Y.; Louis S. Kucera, Pfafftown, N.C.

[73] Assignees: Wake Forest University, Winston-Salem; University of North Carolina at Chapel Hill, Chapel Hill, both of N.C.

[21] Appl. No.: 418,853

[22] Filed: Apr. 7, 1995

Related U.S. Application Data

[63] Continuation of Ser. No. 955,709, filed as PCT/US91/04289, Jun. 14, 1991, abandoned.

[51] Int. Cl.$^6$ ..................................................... C07H 19/20
[52] U.S. Cl. .................... 536/26.1; 536/26.2; 536/26.21; 536/26.22; 536/26.23; 536/26.7; 536/26.8; 536/115; 536/117; 536/120
[58] Field of Search ............................... 536/26.2, 26.23, 536/26.5, 26.7, 26.8, 115, 117, 120, 26.1, 26.13

[56] References Cited

U.S. PATENT DOCUMENTS

| | | | |
|---|---|---|---|
| 4,291,024 | 9/1981 | Turcotte | 424/180 |
| 4,471,113 | 9/1984 | MacCross | 536/28.5 |
| 4,622,392 | 11/1986 | Hong et al. | 536/28.5 |
| 4,724,232 | 2/1988 | Rideout et al. | 514/50 |
| 4,797,479 | 1/1989 | Shuto et al. | 536/28.5 |
| 4,921,951 | 5/1990 | Shuto et al. | 536/28.5 |
| 5,138,045 | 8/1992 | Cook et al. | 536/23.1 |
| 5,223,263 | 6/1993 | Hostetler et al. | 514/45 |

FOREIGN PATENT DOCUMENTS

| | | |
|---|---|---|
| 61-238793 | 10/1986 | Japan. |
| 9000555 | 1/1990 | WIPO. |

OTHER PUBLICATIONS

C. Hong, "Nucleoside Conjugates. 7. Synthesis and Antitumor Activity of 1-β-D-Arabinofuranosylcytosine Conjugates of Ether Lipids," *J. Med. Chem.* 29, 2038 (1986).

C. Hong, "Nucleoside Conjugates. 11. Synthesis and Antitumor Activity of 1-β-D-Arabinofuranosylcytosine and Cytidine Conjugates of Thioether Lipds," *J. Med. Chem.* 33, 1380 (1990).

K. Hostetler et al., "Synthesis and Antiretroviral Activity of Phospholipid Analogs of Azidothymidine and Other Antiviral Nucleosides," *The Journal of Biological Chemistry* 265, No. 11, 6112 (1990).

L. Kucera et al., "Novel Membrane–Interactive Ether Lipid Analogs that Inhibit Infectious HIV-1 Production and Induce Defective Virus Formation," *AIDS Research and Human Retroviruses* 6, No. 4, 491 (1990).

M. MacCoss et al., "Nucleoside–Phospholipid Prodrugs," 4th international Round Table Nucleosides, Nucleotides and their Biological Applications, Antwerp, Feb. 4–6, p. 46 (Feb. 4–6, 1981).

C. Raetz et al., "Phospholipid Derivative of Cytosine Arabinoside and its Conversion to Phosphatidylinositol by Animal Tissue," *Science* 196, 303 (1977).

*Primary Examiner*—Douglas W. Robinson
*Assistant Examiner*—James O. Wilson
*Attorney, Agent, or Firm*—Schwegman, Lundberg, Woessner & Kluth

[57] ABSTRACT

Ether lipid nucleoli covalent conjugates and derivatives thereof are disclosed, along with pharmaceutical compositions containing the same and methods of using the same to combat HIV-1 infections. Illustrative are 3'-Azido-3'-deoxythmidine-5'-monophosphate-D,L-3-octadecanamido-2-ethoxypropane and 3'-Azido-3'-deoxythymidine-5'-butyrate-γ-N,N,N-trimethyl-ammonium-β-(1-phospho-2-ethoxy-3-hexadecyloxypropane).

21 Claims, No Drawings

ETHER LIPID-NUCLEOSIDE COVALENT CONJUGATES

This is a continuation, of application Ser. No. 07/955,709, filed as PCT/US91/04289, Jun. 14, 1991, now abandoned.

FIELD OF THE INVENTION

The present invention relates to antiviral compounds in general, and particularly relates to covalent conjugates of ether lipids and antiviral nucleoside analogs, which conjugates have antiviral activity.

BACKGROUND OF THE INVENTION

The currently preferred treatment for combating human immunodeficiency virus type 1 (HIV-1) infections is by the administration of 3'-azido-3'-deoxythymidine, or AZT, to an afflicted subject. See, e.g., U.S. Pat. No. 4,724,232 to Rideout et al.

C. Piantadosi et al., PCT Appln No. US89 04747 (published May 17, 1990), discloses a method of combating HIV-1 infections which comprises administering various ether lipid compounds in an amount effective to inhibit replication of the virus in infected cells. See also L. Kucera et al., *Aids Research and Human Retroviruses* 6, 491 (1990).

Various lipid derivatives of antiviral nucleosides, and the liposomal incorporation thereof, are disclosed in PCT Application Serial No. WO 90/00555 of K. Hostetler et al. See also K. Hostetler et al., *J. Biol. Chem* 265, 6112, 6113 FIG. 1 (1990).

U.S. Pat. No. 4,291,024 to Turcotte concerns cytotoxic liponucleotide analogs, and U.S. Pat. No. 4,921,951 to Shuto et al. discloses antineoplastic nucleoside-phospholipid conjugates.

In spite of prior efforts, there is an ongoing need for new ways to treat HIV-1 infections. The present invention is based on our continuing research in this area.

SUMMARY OF THE INVENTION

Disclosed herein are ether lipid-nucleoside covalent conjugates (or "lipid-nucleoside conjugates") of Formula (I) below and the salts thereof:

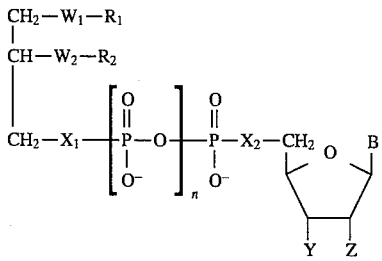

wherein:

$R_1$ is C10–C20 saturated or unsaturated alkyl containing not more than three double bonds. Preferably, $R_1$ is C16–C18 linear alkyl containing not more than one double bond.

$R_2$ is H or C1–C20 saturated or unsaturated alkyl containing not more than three double bonds. Preferably, $R_2$ is H or C1–C3 alkyl.

$W_1$ is S, O, NHC(=O), or NH. Preferably $W_1$ is NHC(=O).

$W_2$ is S, O, NHC(=O), OC(=O), NH, or a covalent bond. Preferably, $W_2$ is O.

n is zero or one.

$X_1$ and $X_2$ are each independently oxygen or a covalent bond, subject to the proviso that when n is zero, then at least either $X_1$ or $X_2$ is O.

Y is H, F, or $N_3$; Z is H or F; or Y and Z together are a covalent bond (i.e., form a didehydro). Preferably, Y is H or $N_3$; Z is H; or Y and Z together are a covalent bond. More preferably, Y is H or $N_3$ and Z is H.

B is a base such as adenine, thymine, cytosine, guanine, hypoxanthine, uracil, 5-fluoro-cytosine, 2-fluoro-adenine, 2-chloro-adenine, 2-bromoadenine, and 2-amino-adenine.

Also disclosed herein are lipid-nucleoside conjugates of Formula (II) below and the salts thereof:

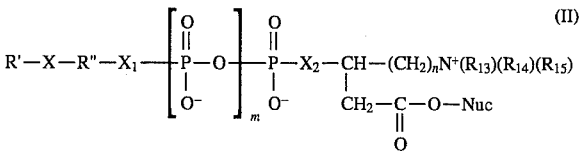

wherein:

X is S, O, NHC(=O), OC(=O), or NH, preferably NHC(=O).

R' is linear or branched, saturated or unsaturated C10–C20 alkyl containing not more than four double bonds, linear or branched, saturated or unsaturated C10–C20 acyl containing not more than four double bonds, phenyl, or naphthyl. More preferably, R' is C14–C20 linear saturated or unsaturated alkyl containing not more than three double bonds. Most preferably, R' is C16–C18 linear alkyl containing not more than one double bond.

R" is C5 to C6 cycloalkylene, or a straight-chained or branched, saturated or unsaturated aliphatic hydrocarbon chain containing 2–8 carbon atoms, which is unsubstituted or substituted one or more times by hydroxyl, phenyl, C1–C20 acyloxy, C1–C20 alkylthio, C1–C20 acylated amino, C1–C20 alkyl, or by C1–C20 alkoxy which is unsubstituted or is substituted by phenyl or C1–C5 alkoxy. Preferably, R" is C2–C4 linear alkyl which is unsubstituted or is substituted one or two times by hydroxyl, phenyl, C1–C20 acyloxy, C1–C20 alkylthio, C1–C20 acylated amino or by C1–C20 alkoxy which is unsubstituted or is substituted by phenyl or C1–C5 alkoxy. More preferably, R" is linear C2–C4 alkyl which is unsubstituted or substituted one or two times by hydroxyl, phenyl, C1–C20 acyloxy, C1–C20 alkylthio, C1–C20 acylated amino or by C1–C20 alkoxy which is unsubstituted or is substituted by phenyl or C1–C5 alkoxy.

m is zero or one.

$X_1$ and $X_2$ are each independently oxygen or a covalent bond, subject to the proviso that when m is zero, then at least either $X_1$ or $X_2$ is O.

n is 1 to 3. Preferably n is 1.

$R_{13}$, $R_{14}$, and $R_{15}$ are each independently either hydrogen or methyl, preferably methyl.

Nuc is:

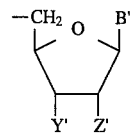

wherein:

Y' is H, F, or $N_3$; Z is H or F; or Y' and Z' together are a covalent bond (i.e., form a didehydro). Preferably, Y' is H or $N_3$; Z' is H; or Y' and Z' together are a covalent bond. More preferably, Y' is H or $N_3$ and Z' is H.

B' is a base such as adenine, thymine, cytosine, guanine, hypoxanthine, uracil, 5-fluoro-cytosine, 2-fluoro-adenine, 2-chloro-adenine, 2-bromo-adenine, and 2-amino-adenine.

A specific example of compounds of Formula (II) above are those of Formula (III) below and the salts thereof:

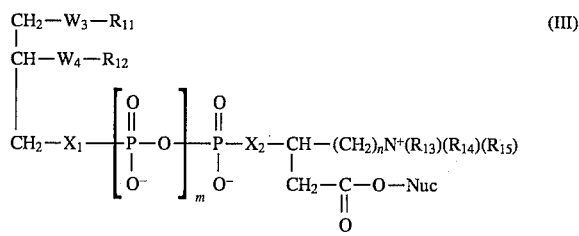

wherein:

$R_{11}$ is C10–C20 saturated or unsaturated alkyl containing not more than three double bonds. Preferably, $R_{11}$ is C16–C18 linear alkyl containing not more than one double bond.

$R_{12}$ is H or C1–C20 saturated or unsaturated alkyl containing not more than three double bonds. Preferably, $R_{12}$ is H or C1–C3 alkyl.

$W_3$ is S, O, NHC(=O), OC(=O), or NH. Preferably $W_3$ is NHC(=O).

$W_4$ is S, O, NHC(=O), OC(=O), NH, or a covalent bond. Preferably, $W_4$ is O.

m is zero or one.

$X_1$ and $X_2$ are each independently oxygen or a covalent bond, subject to the proviso that when m is zero, then at least either $X_1$ or $X2$ is O.

n is 1 to 3. Preferably n is 1.

$R_{13}$, $R_{14}$, and $R_{15}$ are each independently either hydrogen or methyl, preferably methyl.

Nuc is as given in connection with Formula (II) above.

Also disclosed are pharmaceutical compositions comprising a lipid-nucleoside conjugate according to Formula I, II, or III above in a pharmaceutically acceptable carrier, wherein the lipid-nucleoside conjugate is included in the composition in an HIV-1 combating amount.

Also disclosed is the use of a lipid-nucleoside conjugate according to Formula I, II or III above to prepare a pharmaceutical composition or medicament for combating an HIV-1 infection in an afflicted subject.

Also disclosed is a method of combating HIV-1 infections in an afflicted subject comprising administering the subject an effective HIV-1 combating amount of a lipid-nucleoside conjugate according to Formula I, II or III above.

DETAILED DESCRIPTION OF THE INVENTION

Phospholipid-nucleoside conjugates of the present invention (e.g., Compounds A–D) may be prepared according to Scheme 1. The starting alcohols are synthesized as previously described. See. M. Marx et al., *J. Med. Chem.* 31, 858 (1988); S. Morris-Natschke et al., *J. Med. Chem.* 29, 2114 (1986).

SCHEME 1
Phospholipid Nucleoside Conjugates

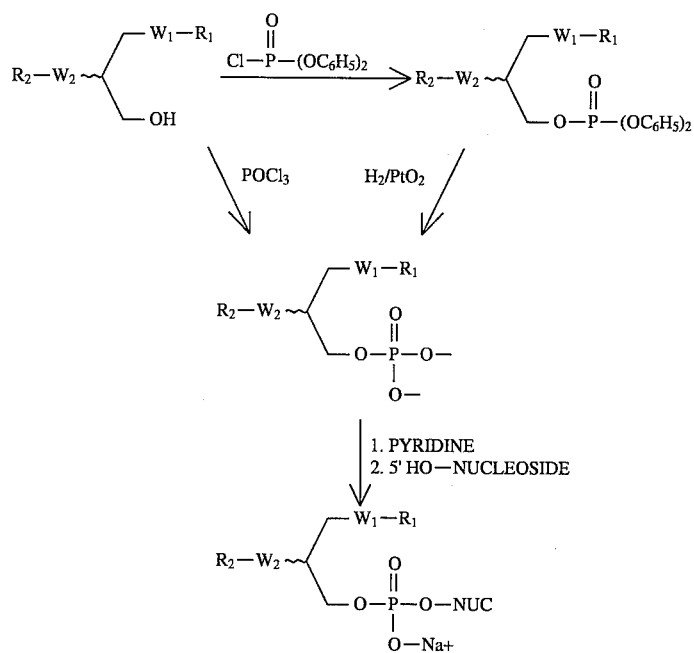

The amidoalkyl glycerol derivative is phosphorylated with diphenylchlorophosphate in pyridine to give the corresponding phosphate ester. See C. Piantadosi, *J. Pharm. Sci.* 62, 320 (1973). The phenyl groups are then removed via hydrogenolysis with $PtO_2$ to give the intermediate. The thio and oxygen ether derivatives are phosphorylated by an alternative procedure using phosphorus oxychloride and triethylamine or pyridine. See *Ether Lipids: Biochemical and Biomedical Aspects*, 403 (H. Mayold and F. Paltauf eds. 1983); C. Hong et al., *J. Med. Chem.* 29, 2038 (1986). The phosphatidic acid derivatives are then conjugated to the 5' hydroxyl of the appropriate nucleoside (NUC) via. dicyclohexylcarbodiimide (DCC) condensation, and subsequent conversion to the sodium salt gave the desired products. See E. Ryu et al., *J. Med. Chem.* 25, 1322 (1982).

The synthesis of the phosphonate analogue (e.g., Compound E) is shown in Scheme 2.

SCHEME 2
Synthesis of Phosphonate-Nucleoside Conjugates

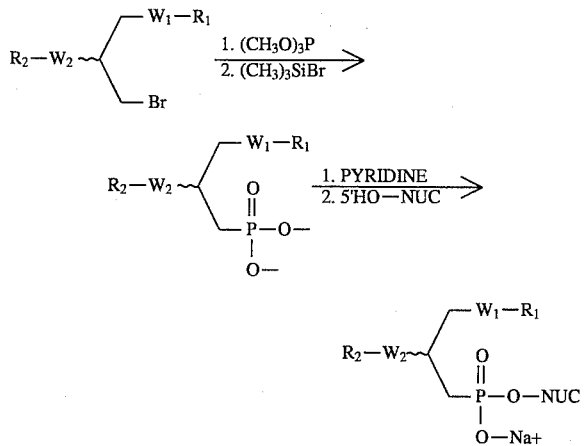

Starting with the appropriate bromopropane, see C. Marasco et al., *J. Med. Chem.* 33,985 (1990), the halide is displaced with trimethylphosphite to afford the corresponding phosphonate. B. Arbuzov, *Pure Appl. Chem.* 9, 307 (1964). The protective methyl groups are then cleaved with trimethylsilylbromide, see R. Bittman et al., *Chem. Phys. Lipids* 34, 201 (1984), to give the expected phosphonic acid. Condensation of the phosphonic acid intermediate with a nucleoside such as AZT is done in the usual manner to give product phosphonate.

The carnitine conjugates (e.g., Compound AA) are prepared according to Scheme 3.

SCHEME 3
Synthesis of Carnitine-Nucleoside Conjugates

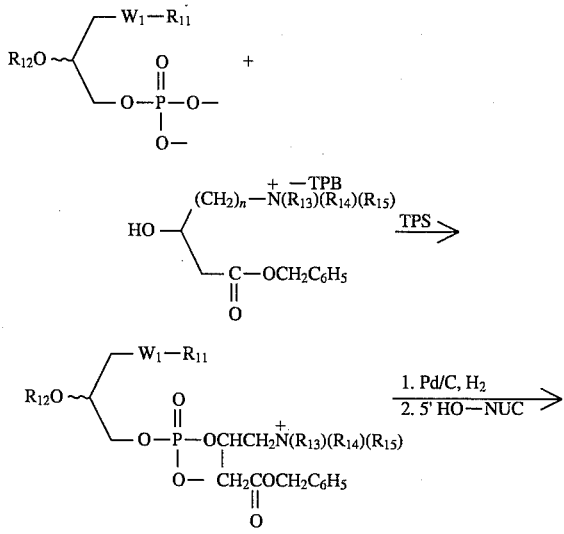

-continued
SCHEME 3
Synthesis of Carnitine-Nucleoside Conjugates

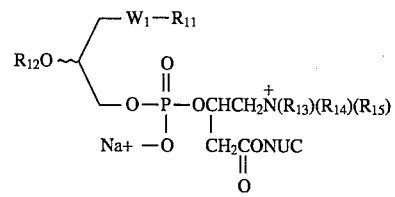

The condensation of the starting intermediate with the benzyl ester of carnitine as the tetraphenylborate salt is done via a 2,4,6-triisopropylbenzenesulfonylchloride (TPS) coupling to give a benzyl esterified carnitine. See U. Hintze and G. Gercken, *Lipids* 10, 20 (1974). The benzyl ester of the esterified intermediate is then cleaved by hydrogenolysis with Pd on activated carbon to yield the free carboxylic acid. Condensation of this intermediate with a nucleoside such as AZT is then performed in the usual manner to give the expected product as the sodium salt.

The pyrophosphate or phosphonophosphate conjugates are synthesized from the condensation of the appropriate dialkyl or amidoalkyl phosphatidic or phosphonic acid derivative with the appropriate 5'-monophosphomorpholidate nucleoside as the N,N'-dicyclohexylcarboxamidinium salt in pyridine. The phosphophosphonate conjugate is synthesized in an analogous manner from the appropriate dialkyl or amido alkyl phosphatidic acid congener and the appropriate 5'-phosphonomorpholidate nucleoside as the N,N'-dicyclohexylcarboxamidinium salt.

In case the compounds disclosed above have an asymmetric carbon atom, the present invention also concerns the enantiomeric forms. The resolution of the racemates into the enantiomeric forms can be done in the last step of the process, or in the appropriate preceding step, by known procedures, for example, by converting the racemate with an optically active reagent into a diasteriomeric pair and subsequent resolution thereof.

Exemplary antiviral nucleosides which may be covalently joined to the 5' carbon on the ribose ring to form lipid-nucleoside conjugates of the present invention include 3'-deoxythymidine; 3'-fluoro-3'-deoxythymidine; 2',3'-dideoxycytidine; 2',3'-dideoxy-5-fluoro-cytidine; 2',3'-dideoxyadenosine; 3'-azido-2',3'-dideoxyadenosine; 2'-fluoro-2',3'-dideoxyadenosine; 2',3'-dideoxy-2-fluoro-adenosine; 2',3'-dideoxy-2-chloro-adenosine; 2',3'-dideoxy-2-bromo-adenosine; 2',3'-dideoxy-2-amino-adenosine; 2',3'-dideoxyguanosine; 3'-azido-2',3'-dideoxyguanosine; 3'-azido-2',3'-dideoxyuridine; 2',3'-didehydro-2',3'-dideoxycytidine, and 2',3'-didehydro-2',3'-dideoxythymidine. See generally H. Mitsuya et al., *Proc. Natl. Acad. Sci. USA* 82, 7096 (1985); H. Mitsuya and S. Broder. *Proc. Natl. Acad Sci. USA* 83, 1911 (1986); P. Herdewijn et al.; *J. Med. Chem.* 30, 1276 (1987); C-H. Kim et al., *J. Med. Chem.* 30, 862 (1987); V. Marquez et al., *Biol. Chem. Pharm.* 36, 2719 (1987); T. Haertle et al., *J. Cellular Biochem. Suppl.* 11D, 65 (1987); J. Balzarini et al., *Biochem. Biophys. Res. Comm.* 145 277 (1987); M. Baba et al., *Biochem. Biophys. Res. Comm.* 145, 1080 (1987); R. Schinazi et al., *J. Cellular Biochem. Suppl.* 11D, 74 (1987); Y. Hamamoto et al., *Antimicrob. Agents and Chemother.* 31, 907 (1987). Conjugates of 3'-Azido-3'-deoxythymidine are preferred.

The following compounds are illustrative of the compounds of Formula I above. These compounds may be prepared by the procedures described herein, or by variations thereof which will be apparent to those skilled in the art in light of the instant disclosure.

(A) 3,-azido-3'-deoxythymidine- 5'-monophosphate-D,L- 3-octadecanamido-2-ethoxypropane;

(B) 3'-azido-3'deoxythymidine-5'-monophosphate-D,L- 3-hexadecyloxy-2-ethoxypropane;

(C) 3'azido-3'-deoxythymidine-5'-monophosphate-D,L- 3-hexadecylthio-2-methoxypropane;

(D) 2,3,-dideoxyinosine-5'-monophosphate-D,L- 3-octadecanamido-2-ethoxypropane;

(E) 3'-Azido-3'-deoxythymidine-5'-phosphono-D,L- 3-hexadecyloxy-2-methoxypropane;

(F) 3'-Azido-3'-deoxythymidine-5'-monophosphate-D,L- 3-octadecanamido-2-hexadecyloxypropane;

(G) 3'-Azido-3'-deoxythymidine-5'-monophosphate-D,L- 3-octadecanamido-2-palmitoylpropane;

(H) 3'-Azido-3-deoxythymidine-5'-diphosphate-D,L- 3-octadecanamido-2-ethoxypropane;

(I) 3'-Azido-3'-deoxythymidine-5'-phospho-1- phosphono-D,L- 3-octadecanamido-2-ethoxypropane;

(J) 3-Azido-3'-deoxythymidine-5'phosphono-1-phospho-D,L- 3-octadecanamido-2-ethoxypropane;

(K) 3'-deoxythymidine-5'-monophosphate-D,L-octadecanamido-2-ethoxypropane;

(L) 3'-fluoro-3'-deoxythymidine-5'-monophosphate-D,L- 3-hexadecyloxy-2-ethoxypropane;

(M) 2',3'-dideoxycytidine-5'-monophosphate-D,L- 3-hexadecylthio-2-methoxypropane;

(N) 2',3'-dideoxy-5-fluoro-cytidine-5'-monophosphate-D, L- 3-octadecanamido-2-ethoxypropane;

(O) 2',3'-dideoxyadenosine-5'-phosphono-D,L-hexadecyloxy-2-methoxypropane;

(P) 3'-Azido-2',3'-dideoxyadenosine-5'-monophosphate-D,L- 3-octadecanamido-2-hexadecanoylpropane;

(Q) 3'-Azido-2',3'-dideoxyadenosine-5'-monophosphate-D,L- 3-octadecanamido-2-palmitoylpropane;

(R) 2'-fluoro-2',3'-dideoxyadenosine-5'-diphosphate-D,L- 3-octadecanamido-2-ethoxypropane;

(S) 2',3'-didehydro-2',3'-dideoxycytidine-5'-phospho-1-phosphono-D,L-3-octadecanamido-2-ethoxypropane;

(T) 3'-Azido-2',3'-dideoxyuridine-5'-phosphono- 1-phospho-D,L-3-octadecanamido-2-ethoxypropane;

(U) 2',3'-Dideoxy-2-fluoro-adenosine-5'-monophosphate-D,L- 3-octadecanamido-2-ethylpropane;

(V) 2',3'-Dideoxy-2-chloro-adenosine-5'-monophosphate-D,L- 3-hexadecyloxy-2-ethylpropane;

(W) 2',3'-Dideoxy-2-amino-adenosine-5'-monophosphate-D,L- 3-hexadecylthio-2-hexadecylthiopropane;

(X) 2',3'-Dideoxy-2-bromo-adenosine-5,-monophosphate-D,L- 3-octadecanamido-2octadecanamidopropane;

(Y) 2',3'-Dideoxyguanosine-5'-phosphono-D,L-3-hexadecylamino-2-hexadecylaminopropane;

(Z) 3'-Azido-2',3'-dideoxyguanosine-5,-monophosphate-D,L- 3-octadecanamino-2-hexadecyloxypropane; and (A') 3'-Azido-3'-deoxythymidine-5'-diphosphate-D,L- 3-hexadecyloxy-2-ethoxypropane.

The following compounds are illustrative of the compounds of Formula II above. These compounds may likewise be prepared by the procedures described herein, or variations thereof which will be apparent to those skilled in the art in light of the present disclosure.

(AA) 3'-Azido-3'-deoxythymidine- 5'-butyrate-γ-N,N,N-trimethyl-ammonium-β-(1-phospho-2-ethoxy-3-hexadecyloxypropane); and (BB) 3'-Azido-3-deoxythymidine- 5'-butyrate-γ-N,N,N-trimethyl-ammonium-β-( 1-phospho-2-ethoxy-3octadecanamidopropane).

The lipid-nucleoside conjugates disclosed herein can be prepared in the form of their pharmaceutically acceptable salts or their non-pharphaceutically acceptable salts. The non-pharmaceutically acceptable salts are useful as intermediates for the preparation of a pharmaceutically acceptable salt pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

The lipid-nucleoside conjugates described above can be combined with an inert pharmaceutical carrier to provide a pharmaceutical composition for enteral or parenteral administration. The compounds described above being the active ingredient in these compositions, they should be included in an amount effective to accomplish the intended treatment. For the preparation of these compositions, use can be made of pharmaceutical carriers adapted for all conventional forms of administration, for example, tablets, capsules, dragees, syrups, solutions, suspensions and the like. As injection medium, it is preferred to use water which contains the additives usual in the case of injection solutions, such as stabilizing agents, solubilizing agents and/or buffers. Additives of this kind include, for example, human serum albumin and synthetic analogs thereof, tartrate and citrate buffers, ethanol, complex formers (such as ethylenediaminetetraacetic acid and the non-toxic salts thereof) and high molecular weight polymers (such as liquid polyethylene oxide) for viscosity regulation. Liquid carrier materials for injection solutions must be sterile and are preferably placed into ampules. Solid carrier materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

A method of combating human immunodeficiency virus Type 1 (HIV-1) infection in an afflicted subject comprises administering to the subject a lipid-nucleoside conjugate as described herein in an amount effective to inhibit replication of infectious virus in the subject. Likewise, a method of combating human immunodeficiency virus Type 1 (HIV-1) infection of cells comprises administering to the cells a lipid-nucleoside conjugate as described herein in an amount effective to inhibit replication of the virus in the cells. Administration of the lipid-nucleoside conjugate to an afflicted subject can be carried out by any suitable means, such as by intravenous administration, intraperitoneal administration, subcutaneous administration, and oral administration.

The dosage of lipid-nucleoside conjugate to be administered depends upon a variety of factors, such as mode of administration, species, age, and subject condition. Usually, the dosage to be administered is from about 0.05 to about 100 milligrams per kilogram of body weight, more preferably between about .1 and about 75 milligrams per kilogram of body weight, and most preferably between about 0.5 and about 50 milligrams per kilogram of body weight.

In the Examples below, proton nuclear magnetic reasonance spectra were recorded in CDCl$_3$ on either a BRUKER 300-MH$_2$ or a VARIAN 400-MH$_2$ spectrometer. Chemical shifts are reported in parts per million relative to internal tetramethylsilane. Infrared spectra were recorded on a Perkin-Elmer 1320 spectrometer as thin films. Melting points were determined on a Thomas-Hoover capillary melting point apparatus and are uncorrected. Microanalyses were performed by Atlantic Microlab Inc. Mass spectral data was obtained from a VG7OS Mass spectrometer. All reactions were performed under a positive pressure of dry nitrogen with dry solvents. Tetrahydrofuran (THF) was distilled from Na and benzophenone, dichloromethane (DCM) from phosphorus pentoxide, triethylamine (Et$_3$N) from KOH, and pyridine was stored over KOH. Chromatographic purification was performed using silica gel 60 (230–400 mesh). Thin layer chromatographic plates were visualized by iodine vapor, molybdenum phosphate spray, and charring following sulfuric acid spray.

EXAMPLE 1

(±-3-Octadecanamido-2-ethoxypropyl-diphenylphosphate. To a three-neck round-bottom flask equipped with a magnetic stir bar, nitrogen inlet and reflux condenser was added a solution of (0.7 mL, 3.39 mmol) diphenylchlorophosphate in 10 mL anhydrous ether. The solution was cooled to 4° C., and a solution of the starting amidoalkyl glycerol[1] (1.0 g, 2.6 mmol) in 15 mL of pyridine and 5 mL of ether was then added. The solution was warmed to room temperature, and then heated to 52° C. for 3 h. After cooling to room temperature, the reaction mixture was diluted with 50 mL of ether, extracted twice with 25 mL portions of distilled water, once with 25 mL of cold 0.5N HCl, and once with 25 mL of distilled water. The ether layer was dried over sodium sulfate, filtered, and concentrated in vacuo to give a pale yellow oil. Purification by silica gel chromatography (discontinuous gradient of hexane:ethyl acetate 10:1 to 1:1 as eluent) gave 961 mg of pure product (60.1%). $^1$H-NMR (CDCl$_3$): δ0.87 (t, 3H, terminal methyl), 1.1–1.3 [m, 31H, (CH$_2$)$_{14}$, CH$_3$CH$_2$O], 1.55 (m, 2H, NH—C—CH$_2$CH$_2$), 2.15 (t, 2H, NH—C—CH$_2$), 3.3–3.6 (m, 5H, CH$_3$CH$_2$O CHCH$_2$NH), 4.25 (m, 2H, CH$_2$OP), 5.9 (t, 1H, NH), 7.15–7.35 [m, 10 H, (OC$_6$H$_5$)$_2$].

EXAMPLE 2

(±)-3-Octadenanamido-2-ethoxypropyl-phospatidic acid. Into a Parr hydrogenation bottle was placed a solution of 500 mg of (±)-3-Octadecanamido-2-ethoxypropyldiphenylphosphate prepared according to Example 1 above in 100 mL of absolute ethanol. To the solution was added 69 mg of PtO$_2$, before placement onto the hydrogenation apparatus. The reaction mixture was placed under 14.5 psi of hydrogen, and shaken at room temperature. After 100 mins, 6 psi had been consumed, and TLC (CHCl$_3$:MeOH:H$_2$O, 70:35:4) indicated the absence of starting material. The reaction mixture was suction filtered through Celite, and the ethanol removed in vacuo. The resulting oil was taken up in 25 mL of pyridine, concentrated in vacuo, and dried under vacuum to give 352 mg (93.3%) Of pure product as a fine powder. 1H-NMR (CDCl$_3$): δ0.87 (t, 3H, terminal methyl), 1.1–1.3 [m, 31H, (CH$_2$)$_{14}$, CH$_3$CH$_2$O], 1.55 (m, 2H, NH—C—CH$_2$CH$_2$), 2.25 (t, 2H, NH—C—CH$_2$), 3.3–3.75 (m, 5H, CH$_3$CH$_2$OCHCH$_2$NH), 4.15 (m, 2H, CH$_2$OP), 6.7 (t, 1H, NH).

EXAMPLE 3

(±)-3-Hexadecyloxy-2-ethoxypropyl-phosphatidic acid. To a three-neck round-bottom flask equipped with a magnetic stir bar, nitrogen inlet, and reflux condenser was added a solution of phosphorus oxychloride (0.62 mL, 6.6 mmol) in 5 mL of THF. The solution was cooled to 0° C., and a solution of the starting dialkylglycerol (2.0 g, 5.8 mmol), and pyridine (1.4 mL, 17.3 mmol) in 15 mL of THF were added. The reaction mixture was maintained at 0° C. for 3 h, and then 10 mL of 10% sodium bicarbonate was added. The mixture was stirred an additional 20 min, and poured into 30 mL of ice water. The solution was acidified by the dropwise addition of 2N HCl, and then extracted twice with 30 mL portions of ether. The ether layer was dried over sodium sulfate, filtered, concentrated in vacuo, taken up in 100 mL of pyridine, concentrated, and dried under vacuum to give 1.5 g (46%) of product as a waxy solid. $^1$H-NMR (CDCl$_3$): δ0.87 (t, 3H, terminal methyl), 1.1–1.3 [m, 29H, (CH$_2$)$_{13}$, CH$_3$CH$_2$O], 1.4 (m, 2H, OCH$_2$CH$_2$), 3.4–3.7 (m, 7H, CH$_3$CH$_2$OCHCH$_2$OCH$_2$), 3.85 (m, 2H, CH$_2$OP).

EXAMPLE 4

(±)-3-Hexadecylthio-2-methoxtpropyl-phosphatidic acid. To a three-neck round-bottom flask equipped with a magnetic stir bar, nitrogen inlet, and relux condenser was added a solution of phosphorus oxychloride (0.6 mL, 7 mmol) in 1 mL of hexane. The solution was cooled to 0° C., and a solution of triethylamine (1 mL, 10 mmol) in 1 mL of hexane was added dropwise. The starting thioalkyl glycerol[2] (1.6 g, 5 mmol) was azeotropically dried with toluene, and the volume reduced to 10 mL. This was then added dropwise to the POCl$_3$/Et$_3$N solution, and stirred overnight at room temperature. One mL of water was added to the reaction mixture and stirred for 1 h. The reaction mixture was diluted with 20 mL of water, and extracted twice with 25 mL portions of ether. The organic layers were collected, dried over sodium sulfate, filtered, and concentrated in vacuo. The resulting oil was taken up into 50 mL of pyridine, heated to 50° C. for 2 h, and concentrated in vacuo. Silica gel chromatography (CHCl$_3$:MeOH:NH$_4$OH, 70:35:1 to 70:35:7 as eluent) gave 535 mg of product. $^1$H-NMR (CDCl$_3$): δ0.87 (t, 3H, terminal methyl), 1.2 [bs, 26H, (CH$_2$)$_{13}$], 1.4 (m, 2H, SCH$_2$CH$_2$), 2.4 (t, 2H SCH$_2$CH$_2$), 2.5 (m, 2H, CHCH$_2$S), 3.4–3.7 (m, 4H, CH$_3$OCHCH$_2$S), 4.0 (bm, 2H CH$_2$OP).

EXAMPLE 5

3'-Azido-3'-deoxythynidine-5'-monophosphate-D,L-3-octadecanamido-2-ethoxypropane (Compound A). Into a 25 mL round-bottom flask were placed (±)- 3-Octadenanamido-2-ethoxypropylphospatidic acid (100 mg, 0.22 mmol ) and AZT (43 mg, 0.16 mmol ). The two reactants were then azeotropically dried by the vacuo removal of 3 mL of pyridine three times. To this slurry dicyclohexylcarbodiimide (220 mg, 1.07 mmol) was added, and once again the reactants were azeotropically dried four times with 3 mL portions of pyridine. The solution was then diluted to a final volume of 3 the round bottom flask stoppered, and placed in a desiccator for 4 days. One g of water was added to the reaction mixture, and stirred at room temperature for 4 h. The solvents were removed in vacuo, and the resulting wax purified by silica gel chromatography (gradient of $CHCl_3$:MeOH, 15:1 to 2:1 as eluent) to give pure product. The product was dissolved in 11 mL $CHCl_3$:MeOH: $H_2O$ (4:6:1), placed in a round bottom flask and stirred with 1.5 g of Whatman Pre-Swollen Microgranular Cation (Na+) Exchange Carboxymethyl Cellulose Resin for 1 h. The resin was filtered, and the filtrate concentrated in vacuo to give 32 product as the sodium salt (21%). $^1$H-NMR ($CDCl_3$) : δ0.87 (t, 3H, terminal methyl), 1.1–1.3 [m, 31H, $(\underline{CH}_2)_{14}$, $\underline{CH}_3CH_2O$], 1.55 (m, 2H, NH—C—$CH_2\underline{CH}_2$), 1.8 (s, 3H, Thymidine $CH_3$), 2.1 (t, 2H, NH—C—$\underline{CH}_2$), 2.2 (m, 2H, Thymidine 2' $CH_2$), 3.2–3.5 (m, 5H, $CH_3\underline{CH}_2O$ $\underline{CH}CH_2NH$), 3.75 (m, 2H, $\underline{CH}_2OP$), 3.85 (m, 1H, Thymidine 4' $\underline{CH}$), 3.95 (m, 2H, Thymidine 5' $\underline{CH}_2$), 4.35 (m, 1H, Thymidine 3' $\underline{CH}$), 6.1 (m, 1H, Thymidine 1' $\underline{CH}$), 6.95 (t, 1H, $\underline{NH}$), 7.4 (s, 1H, Thymidine $c_6$ proton), 11.3 (bs, 1H, diimide NH). FAB Mass Spectrum (M+2Na)$^+$; Theoretical 759.3795, Observed 759.3839 (2.0 ppm).

EXAMPLE 6

3'-Azido-3'-deoxthymidine-5'-monophosphate-D.L-3-hexadecyloxy-2-ethoxypropane (Compound B). This analogue was made in analogous manner to that of 3'-Azido-3'-deoxythymidine-5'-monophosphate-D,L- 3-octadecanamido-2-ethoxypropoane from 110 mg of (±)-3-Hexadecyloxy-2 -ethoxypropylphosphatidic acid (0.26 mmol), 50 mg of AZT (0.19 mmol), and 250 mg of DCC (1.24 mmol) to give 37 mg of pure product (28%). $^1$H-NMR ($CDCl_3$): δ0.87 (t, 3H, terminal methyl), 1.1–1.3 [m, 29 H, $(\underline{CH}_2)_{13}$, $\underline{CH}3CH_2O$], 1.5 (m, 2O$CH_2\underline{CH}_2$), 1.8 (s, 3H, Thymidine $CH_3$), 2.25 (.m, 2H, Thymidine 2'$CH_2$), 3.2–3.5 (m, 7H, $CH_3\underline{CH}_2O\underline{CH}CH_2O\underline{CH}_2$), 3.8 (m, 2H, $\underline{CH}_2OP$), 3.9 (m, 1H, Thymidine 4' $\underline{CH}$), 3.95 (m, 2H, Thymidine 5' $\underline{CH}_2$), 4.35 (m, 1H, Thymidine 3' $\underline{CH}$), 6.1 (m, 1H, Thymidine 1' $\underline{CH}$), 7.4 (s, 1H, Thymidine $C_6$ proton), 11.3 (bs, 1H, diimide NH). FAB Mass Spectrum (MH+Na)$^+$; Theoretical 696.3713, Observed 696.3861 (4.6 ppm).

EXAMPLE 7

3'-Azido-3'-deoxythymidine-5'-monophosphate-D,L-3-hexadecylthio-a-methoxypropane (Compound C). This analogue was made in analogous manner to that of 3'-Azido-3'-deoxythymidine-5'-monophosphate-D,L-3-octadecanamido-2-ethoxypropane (from 87 mg of (±)-3-hexadecylthio-2-ethoxypropyl phosphatidic acid (0.20 mmol), 43 mg of AZT (0.16 mmol), and 227 mg of DCC (1.1 mmol) to give 32 mg of pure product (23% ). $^1$H-NMR ($CDCl_3$): δ0.87 (t, 3H, terminal methyl), 1.1–1.3 [m, 26H, $(\underline{CH}_2)_{13}$], 1.45 (m, 2H, $SCH_2\underline{CH}_2$), 1.8 (s, 3H, Thymidine $CH_3$), 2.25 (m, 2H, Thymidine 2' $CH_2$), 2.4 (t, 2H, S—$\underline{CH}_2$), 2.6 (d, 2H, $\underline{CH}_2$—S), 3.3 (s, 3H, $\underline{CH}_3O$), 3.5 (m, 1H, $CH_3O\underline{CH}$), 3.9–4.1 (m, 5H, $\underline{CH}_2OP$, Thymidine 4' $\underline{CH}$, 5' $\underline{CH}_2$), 4.4 (m, 1H, Thymidine 3' $\underline{CH}$), 6.1 (m, 1H, Thymidine 1' $\underline{CH}$), 7.4 (s, 1H, Thymidine $C_6$ proton), 11.3 (bs, 1H, diimide NH). FAB Mass Spectrum (MH+Na)$^+$; Theoretical 698.3328, Observed 698.3344 (2.2 ppm).

EXAMPLE 8

2', 3'-dideoxyinosine-5'-monophosphate-D,L- 3-octadecanamido-2-ethoxypropane (Compound D). This analogue was made in analogous manner to that of 3'Azido-3'-deoxythymidine-5'-monophosphate-D, L-3-octadecanamido-2-ethoxypropane from 92 mg of (±)-3-Octadenanamido-2-ethoxypropyl phospatidic acid (0.20 mmol), 35 mg of DDI (0.15 mmol), and 200 mg of DCC (1.0 mmol) to give 23 mg of pure product (22%). $^1$H-NMR ($CDCl_3$); δ0.87 (t, 3H, terminal methyl), 1.1–1.3 [m, 31H, $(\underline{CH}_2)_{14}$, $\underline{CH}hd 3CH_2$], 1.55 (m, 2H, NH—C—$CH_2\underline{CH}_2$), 1.7 (m, 2H Inosine 2' $\underline{CH}_2$), 2.1 (m, 4H, NH—C—$\underline{CH}_2$, Inosine 3' $\underline{CH}_2$), 3.1–4.1 (m, 10H, $CH_3\underline{CH}_2O\underline{CH}CH_2NH$, $\underline{CH}_2OP$, Inosine 4' $\underline{CH}$, 5' $\underline{CH}_2$), 6.1 (m, 1H, Inosine 1' $\underline{CH}$), 6.95 (t, 1H, $\underline{NH}$), 7.4 (s, 1H, Inosine $C_8$ proton), 11.3 (bs, 1H, diimide NH). FAB Mass Spectrum (M+2Na)$^+$; Theorectical 728.3739, Observed 728.3738 (0.2 ppm).

EXAMPLE 9

(±)-3-Hexadecyloxy-2-methoxypropyl dimethylphosphonate. Into a three-neck round-bottom flask equipped with a magnetic stir bar, nitrogen inlet, and reflux condenser was placed a solution of the starting dialkyl halide, (954 mg, 2.4 mmol) in trimethylphosphite (4.987 g, 30.2 mmol). The solution was heated to 120° C. for 90 h with continuous stirring. The reaction mixture was cooled to room temperature, reduced in vacuo, and purified by silica gel chromatography (gradient of petroleum ether:ether, 10:1 to 1:1 as eluent) to give 741 mg of product (80%) as a yellow viscous oil. $^1$H-NMR ($CDCl_3$): δ0.87 (t, 3H, terminal methyl), 1.1–1.3 [m, 26H, $(\underline{CH}_2)_{13}$], 1.57 (m, 2H, $OCH_2\underline{CH}_2$), 2.08 (m, 2H, $\underline{CH}_2$—P), 3.4–3.6 (m, 7H, $\underline{CH}_3OCH\underline{CH}_2OCH_2$), 3.75 [m, 7H, $CH_3O\underline{CH}$, $P(O\underline{CH}_3)_2$].

EXAMPLE 10

(±)-3-Hexadecyloxy-2-methoxypropyl phosphonic acid. To a three-neck round-bottom flask equipped with a magnetic stir bar, nitrogen inlet, and reflux condenser was added a solution of 6 (740 mg, 1.92 mmol) in 10 mL of alcohol-free chloroform. To this solution bromotrimethylsilane (1.6 g, 10.6 mmol) was added dropwise. After 1 h the solvents were removed in vacuo, and the resulting oil taken up in 25 mL of THF: $H_2O$ (8:2), and stirred overnight at room temperature. The solvents were removed in vacuo, and the residue recrystallized from ether:acetonitrile (1:5) to give 577 mg of pure product (85%) as a white solid (MP 59°–61° C.). The product was taken up into 50 mL of pyridine, the pyridine removed in vacuo, and then dried under vacuum. $^1$H-NMR ($CDCl_3$): δ0.87 (t, 3H, terminal methyl), 1.1–1.3 [m, 26H, $(\underline{CH}_2)_{13}$], 1.57 (m, 2H, $OCH_2\underline{CH}_2$), 2.12 (m, 2H, $\underline{CH}_2$—P), 3.4–3.6 (m, 7H, $\underline{CH}_3OCH\underline{CH}_2OCH_2$), 3.75 (m, 1H, $CH_3O\underline{CH}$).

EXAMPLE 11

3'-Azido-3'-deoxythymidine-5'-phosphono-D,L-3-hexadecyloxy-2-methoxypropane (Compound E). This analogue was made in analogous manner to that of 3'-Azido- 3'-deoxythymidine-5'-monophosphate-D, L-3-octadec-anamido-2-ethoxypropoane from 100 mg of (±)-3-Hexadecyloxy-2-O-methoxypropyl phosphonic acid (0.26 mmol), 50 mg of AZT (0.19 mmol), and 250 mg of DCC (1.24 mmol) to give 29 mg of pure product (23%). $^1$H-NMR ($CDCl_3$): δ0.87 (t, 3H, terminal methyl), 1.1–1.3 [m, 29H, $(\underline{CH}_2)_{13}$, $\underline{CH}CH_2O$], 1.5 (m, 2H, $OCH_2\underline{CH}_2$), 1.8 (s, 3H, Thymidine $CH_3$), 2.25 (m, 2H, Thymidine 2' $CH_2$), 3.2–3.5 (m, 7H, $CH_3\underline{CH}_2OCH\underline{CH}_2OCH_2$), 3.7 (m, 2H, $\underline{CH}_2P$), 3.9 (m, 1H, Thymidine 4' $\underline{CH}$), 3.95 (m, 2H, Thymidine 5' $\underline{CH}_2$), 4.4 (m, 1H, Thymidine 3' $\underline{CH}$), 6.1 (m, 1H, Thymidine 1' $\underline{CH}$), 7.4 (s, 1H, Thymidine $C_6$ proton), 11.3 (bs, 1 H, diimide NH). FAB Mass Spectrum (M+Na)$^+$; Theorectical 688.3426, Observed 688.3437 (1.6 ppm).

EXAMPLE 12

(±)-3-Hexadecylory-2-ethoxypropyl-phosphophocarnitine benzyl ester. To a three-neck round-bottom flask equipped with a magnetic stir bar, nitrogen inlet, and reflux condenser a solution (243 mg, 0.45 mmol) of (±)-3-hexadecyloxy-2-ethoxypropyl-phospatidic acid in 10 mL of pyridine was added. To this solution 778 mg (1.36 mmol) of the benzyl ester of carnitine as the tetraphenylborate salt[9], 412 mg (1.36 mmol) of 2,4,6-triisopropylbenzenesulfoyl chloride, and an additional 15 mL of pyridine were added. The reaction mixture was stirred continuously overnight at room temperature. To the reaction mixture 2.5 mL of distilled water was added, and stirring was continued for 1 h. The solvents were removed in vacuo, and the pale pink oil extracted three times with 30 mL portions of ether. The extract was cooled to 0° C. for 4 h, filtered, and concentrated in vacuo. The resultant yellow oil was purified by silica gel chromatography (gradient $CHCl_3$:MeOH, 10:1 to 1:1) to give 180 mg of pure product (56%). $^1$H-NMR ($CDCl_3$): $\delta 0.87$ (t, 3H, terminal methyl), 1.1–1.4 [m, 29H, $(\underline{CH}_2)_{13}$, $\underline{CH}_3CH_2O$ ], 1.5 (m, 2H, $OCH_2\underline{CH}_2$), 2.7 (m, 2H, P—O—CH$\underline{CH}_2$COO—), 3.3–4.3 [m, 18H, $CH_3\underline{CH}_2OCHCH_2O\underline{CH}_2$, $\underline{CH}_2$ $N(\underline{CH}_3)_3$], 3.85 (m, 3H, $\underline{CH}_2OPO\underline{CH}$), 5.1 (m, 2H, $O\underline{CH}_2C_6H_5$), 7.35 (bs, 5H, $\underline{C}_6H_5$).

EXAMPLE 13

(±)-3-Hexadecyloxy-2-ethoxypropyl-phosphophocarnitine. This analogue was made in similar manner to that of (±)-3-Octadenanamido-2-ethoxypropyl phospatidic acid from 110 mg of (±)-3-Hexadecyloxy- 2-ethoxypropyl phosphophocarnitine benzyl ester and a catalytic amount of Pd/C to give 88 mg of product 93%). $^1$H-NMR ($CDCl_3$): $\delta 0.87$ (t, 3H, terminal methyl), 1.1–1.4 [m, 29H, $(\underline{CH}_2)_{13}$, $\underline{CH}_3CH_2O$], 1.5 (m, 2H, $OCH_2\underline{CH}_2$), 2.7 [m, 2H, $\underline{CH}_2N(CH_3)_3$], 3.3–3.7 [m, 18H, $CH_3\underline{CH}_2OCHCH_2$ O $\underline{CH}_2$, P—O—CH$\underline{CH}_2$—COO—, $N(\underline{CH}_3)_3$], 3.95 (m, 3H, $\underline{CH}_2OPO\underline{CH}$).

EXAMPLE 14

3'-Azido-3'-deoxythymidine-5'-α-carboxyphosphocholine-D,L- 3-hexadecyloxy-2-ethoxypropane (Compound AA). This analogue was made in analogous manner to that of 3'-Azido-3'-deoxythymidine-5'-monophosphate-D,L-3-octadecanamido-2-ethoxypropane from 75 mg of (±)-3-Hexadecyloxy-2-ethoxypropyl phosphocarnitine (0.12 mmol), 32 mg of AZT (0.12 mmol), and 160 mg of DCC (0.8 mmol) to give 41 mg of pure product. $^1$H-NMR ($CDCl_3$): $\delta 0.87$ (t, 3H, terminal methyl), 1.1–1.3 [m, 29H, $(\underline{CH}_2)_{13}$, $\underline{CH}_3CH_2O$], 1.5 (m, 2H, $OCH_2\underline{CH}_2$), 1.8 (s, 3H, Thymidine $CH_3$), 2.25 (m, 2H, Thymidine 2' $CH_2$), 2.7 [m, 2H, $\underline{CH}_2N(CH_3)_3$], 3.2–4.0 [m, 24H, $CH_3\underline{CH}_2OCHCH_2OCH_2$, $\underline{CH}_2$ OPO$\underline{CH}CH_2$COO, $N(\underline{CH}_3)_3$, Thymidine 4'$\underline{CH}$, and 5' $\underline{CH}_2$], 4.35 (m, 1H, Thymidine 3' $\underline{CH}$), 6.1 (m, 1H, Thymidine 1' $\underline{CH}$), 7.4 (s, 1H, Thymidine $C_6$ proton), 11.3 (bs, 1H, diimide NH). FAB Mass Spectrum (MH)$^+$; Theoretical 817.4840, Observed 817.4867, 3.2 ppm.

EXAMPLE 15

Anti-HIV1 Activity of Lipid-Nucleoside Conjugates. The inhibitory effects of lipid-nucleoside conjugates on the replication of human immunodeficiency virus type 1 (HIV-1) virus in cells was examined by the plaque assay procedure of L. Kucera et al., *Aids Research and Human Retroviruses* 6, 491 (1990). In brief, CEM-SS cell monolayers were infected with HIV-1. Infected cells were overlaid with RPMI-1640 plus 10% FBS supplemented with different concentrations of inhibitor. AZT and dideoxyinosine (DDI) were used as positive controls. Plaques were counted at five days after infection. In this assay HIV-1 syncytial plaques are seen as large, multicellular foci (10 to 25 nuclei/syncytium) that appear either brown and granular or clear. Silnce the number of HIV-1 syncytial plaques correlates with reverse transcriptase (RT) and p24 core antigen activity in the HIV-1 infected cell overlay fluids, the syncytial plaque assay can be used to quantify the amount of infectious virus. Reverse transcriptase activity was assayed according to a described procedure (B. J. Poeisz et al., *Proc. Natl. Acad. Sci.* (U.S.A.) 77, 7415 (1980)). The activity of p24 core antigen induced by HIV-1 infection of CEM-SS cells was measured spectrophotometrically using the commercial Coulter EIA.

The results (Table 1) showed that all the lipid-nucleoside conjugates tested have an $IC_{50}$ against HIV-1 syncytial plaque formation ranging from 0.02 to 1.56 μM. The conjugates $IC_{50}$ for cell cytotoxicity ranged from 25.2 to >100 μM. Of interest are data indicating that the differential selectivity for the conjugates ranged from >64 to 1793 compared to 1400 for AZT and >59 for DDI. The highest differential selectivity (1793) was obtained with the amidoalkyl lipid-AZT conjugate. The increased differential selectivity of the amidoalkyl lipid-AZT conjugate over AZT alone (1400) is due to about a ten-fold decrease in cell cytotoxicity of the amidoalkyl lipid-AZT conjugate ($IC_{50}$= 53.8 μM) compared to AZT ($IC_{50}$=5.6 μM). The differential selectivity of the amidoalkyl lipid-AZT is about ten-fold higher than the phosphatidyl AZT prodrug reported by K. Hostetler et al., *J. Biol. Chem.* 265, 6112 (1990).

TABLE 1

Effect of Nucleoside Analog Alone and Ether Lipid Nucleoside Analog Covalent Conjugates on HIV-1 Plaque Formation and Cell Cytotoxicity

| Compound | Inhibitory Concentration$_{50}$ HIV-1 Plaque Formation | (μM) For: Cell Cytotoxicity | Differential Selectivity[1] |
|---|---|---|---|
| A | 0.03 ± 0.02 | 53.8 ± 7.8 | 1793 |
| D | 1.56 ± 0.8 | >100 | >64 |
| B | 0.03 ± 0.02 | 35.0 ± 2.1 | 1167 |
| C | 0.02 ± 0.01 | 29.2 ± 5.7 | 1465 |
| E | 0.02 ± 0.01 | 25.2 ± 1.1 | 1260 |
| AZT | 0.004 ± 0.001 | 5.6 ± 0.8 | 1400 |
| DDI | 1.7 | >100 | >59 |

[1]Differential selectivity = ratio $IC_{50}$ for cytotoxicity ÷ $IC_{50}$ for HIV-1 plaque formation.

EXAMPLE 16

Anti-HIV-1 Activity of Lipid-Nucleoside Conjugates Over Time. The effect of Compound A on HIV-1 acutely infected H9 cells and persistently infected H9IIIB cells was evaluated by measuring reverse transcriptass (RT) and infectious virus production in supernatant fluids harvested at various times (days) after HIV-1 infection and continuous treatment with compound A. The results (Table 2) indicated that Compound A caused a marked inhibition of both reverse transcriptass (RT) and infectious HIV-1 production in continuously treated and acutely infected H9 cells. In persistently infected H9IIIB cells, Compound A had little effect on RT activity but a marked inhibition of infectious HIV-1 production (Table 2). The best interpretation of these results is that Compound A inhibits reverse transcription and integration of provirus DNA and infectious virus production in HIV-1 acutely infected cells. In persistently infected cells that already have integrated provirus DNA before treatment, Compound A markedly inhibits infectious virus production.

TABLE 2

Effect of Long-Term Amide Ether Livid-AZT Covalent Conjugate (Compound A) Treatment on HIV-1 Replication in Acutely Infected H9 Cells and Persistently H9IIIB Cells

| Condition of Cells | Days Post Treatment | | | | | | |
|---|---|---|---|---|---|---|---|
| | 7 | 14 | 21 | 28 | 35 | 42 | 50 |
| RT DPM (& Inhibition by CP-92) at: | | | | | | | |
| H9 + HIV-1 | 172 | 93,173 | 47,500 | 33,110 | 26,979 | 42,130 | 46,331 |
| H9 + HIV-1 + Compound A | (100) | (100) | (97) | (92) | (97) | (98) | (67) |
| H9IIIB + HIV-1 | 11,045 | 17,788 | 22,660 | 22,056 | 32,708 | 46,881 | 32,237 |
| H9IIIB + HIV-1 + Compound A | (0) | (18) | (33) | (0) | (26) | (28) | (0) |
| Syncytial Plaque Count Per ML (% Inhibition by CP-92) at: | | | | | | | |
| H9 + HIV-1 | 346 | 20,640 | 11,042 | 6,986 | 3,894 | ND[1] | ND |
| H9 + HIV-1 + Compound A | (43) | (98) | (96) | (94) | (95) | ND | ND |
| H9IIIB + HIV-1 | 7,706 | 6,638 | 8,960 | 8,000 | 12,450 | ND | ND |
| H9IIIB + HIV-1 + Compound A | (87) | (91) | (91) | (89) | (95) | ND | ND |

[1]Not determined.

EXAMPLE 17

Anti-HIV1 Activity of Lipid-Nucleoside Conjugates in Monocyte/Macrophages. Monocyte/macrophages represent a major reservoir of HIV-1 in the infected human host. See L. Epstein et al., *AIDS Res.* 14, 447 (1984). However, these cells tend to be resistant to dideoxynucleoside prodrugs due to low levels of kinases needed to activate the prodrugs. See C. Perno et al., *J. Exp. Med.* 168, 1111 (1984). To test the compounds of the present invention in these cells, we treated HIV-1 persistently infected monocyte/macrophage (U1) cells with AZT and Compound A and measured the effect on HIV-1 replication. The results (Table 3) indicate that the compounds did not significantly inhibit HIV-1 induced RT and p24 core antigen production. As expected, AZT alone caused only 13% inhibition of infectious HIV-1 production. However, Compound A inhibited infectious HIV-1 production by 33%.

TABLE 3

Effect of AZT and Lipid-Nucleoside Conjugate on HIV-1 Induced RT, p24 Core Antigen Synthesis and Infectious Virus Production in Persistently Infected Monocyte/Macrophage Cells

| Compound | (RT DPM) | Percent of Control (p24 core Ag) | (PFU) |
|---|---|---|---|
| Control | (79,328) 100 | (94) 100 | (750) 100 |
| + AZT | 90 | 101 | 87 |
| + Compound A | 121 | 84 | 67 |

EXAMPLE 18

(±)-3-Octadecanamido-2-ethoxlpropyl phosphocarnitine benzyl ester. This compound was made in a similar manner to that of (±)-3-hexadecyloxy-2-ethoxypropyl phosphocarnitine benzyl ester from 206 mg of 3-octadecanamido-2-ethoxypropyl phosphatidic acid, 766 mg of the benzyl ester of carnitine as the tetraphenylborate salt, and 400 mg of triisopropylbenzenesulfonyl chloride giving 74 mg of product (32%). $^1$H-NMR (CDCl$_3$): $\delta$0.87 (t, 3H, terminal methyl), 1.1 (t, 3H, OCH$_2$C$\underline{H}_3$), 1.2–1.4 [m, 28H; (C$\underline{H}_2$)$_{14}$], 1.5 (m, 2H, NHCOCH$_2$C$\underline{H}_2$), 2.1 (t, NHCOC$\underline{H}_2$), 2.7 (m, 2H, P—O—CHC$\underline{H}_2$—COO—), 3.0–3.7 [m, 16H, CH$_3$ C$\underline{H}_2$OC$\underline{H}$C$\underline{H}_2$NHCO, C$\underline{H}_2$N(C$\underline{H}_3$)$_3$], 3.9 (m, 3H, C$\underline{H}_2$OPOC$\underline{H}$), 5.1 (m, 2H, OC$\underline{H}_2$C$_6$H$_5$), 6.85 and 6.95 (m, 1H, NH diastereomers), 7.35 (bs, 5H, C$_6$$\underline{H}_5$).

EXAMPLE 19

(±)-3-Octadecanamido-2-ethoxypropyl, phosphocarnitine. The above benzyl ester (74 mg) was hydrogenated at 15 psi using a catalytic amount of Pd/C to give 53 mg of product (83%). $^1$H-NMR (CDCl$_3$): $\delta$0.87 (t, 3H, terminal methyl), 1.1 (t, 3H, OCH$_2$C$\underline{H}_3$), 1.2–1.4 [m, 28H, (C$\underline{H}_2$)$_{14}$, ], 1.5 (m, 2H, NHCOCH$_2$C$\underline{H}_3$), 2.1 (t, NHCO C$\underline{H}_2$), 2.7 (m, 2H, P—O—CHC$\underline{H}_2$—COO—), 3.3–4.0 [m, 18 H, CH$_3$C$\underline{H}_2$OC$\underline{H}$C$\underline{H}_2$NHCO, C$\underline{H}_2$N(C$\underline{H}_3$)$_3$, C$\underline{H}_2$OPOCH), 5.1 (m, 1H, OPOCH), 6.9 (m, 1H, NH).

EXAMPLE 20

3'-Azido-3'-deoxythymidine-5'-α-carboxyphosphocholine-D,L- 3-octadecanamido-2ethoxypropane (compound BB). This analogue was made in analogous manner to that of 3'-azido-3'-deoxythymidine-5'-monophosphate-D,L-3-octadecanamido-2-ethoxypropane from 48 mg of (±)-1-octadecanamido-2-ethoxypropyl phosphocarnitine, 17 mg of AZT, 11 mg of N,N-dimethylaminopyridine, and 87 mg of DCC to give 8 mg of pure product (15% yield). $^1$H-NMR (CDCl$_3$): $\delta$0.87 (t, 3H, terminal methyl), 1.1 (t, 3H, C$\underline{H}_3$O), 1.2–1.4 [m, 28H, (C$\underline{H}_2$)$_{14}$], 1.5 (m, 2H, NHCOCH$_2$ C$\underline{H}_2$), 1.8 (s, 3H, Thymidine CHC$\underline{H}_3$), 2.1 (t, 2H, NHCO C$\underline{H}_2$), 2.2–2.7 (m, 4H, Thymidine 2' C$\underline{H}_2$, P—O—CH C$\underline{H}$C$\underline{H}_2$— COO—), 3.2–4.1 [m, 22H, CH$_3$C$\underline{H}$H$_2$O C$\underline{H}$C$\underline{H}_2$NHCO, C$\underline{H}_2$OPO, C$\underline{H}_2$N(C$\underline{H}_3$)$_3$, Thymidine 4' C$\underline{H}$, and 5' C$\underline{H}_2$], 4.6–5.5 (m, 3H, Thymidine 3' C$\underline{H}$, OPOCH, Thymidine 1' CH), 6.9 (m, 2H, Thymidine C6 proton, NH).

EXAMPLE 21

3'-Azido-3'-deoxythymidine-5'-diphosphate-D,L- 3-octadecanamido-2-ethoxypropane (Compound H). 3-Octadecanamido- 2-ethoxypropyl phosphatidic acid (36 mg, 0.08 mmol) was azeotropically dried with pyridine (3 ml) three times. AZT 5'-monophosphate morpholidate (25 mg, 0.06 mmol) was added and the drying repeated four times. An additional 3 ml of pyridine was added and the reaction allowed to continue for 96 hours at room temperature under nitrogen. After removal of the pyridine under vacuum, the resulting oil was chromatographed on 2 g of silica gel eluting with chloroform:methanol (65:35) to chloroform:methanol:water (65:35:1 to 65:35:4). Impure fractions were collected and rechromatographed using as eluent, chloroform to chloroform:methanol (9: 1 to 2:1) to chloroform: methanol: water (2:1:0.1 to 2: 1: 0.4). The resulting pure product was dissolved in chloroform:methanol:water (4:6:1) and converted to the sodium salt by stirring twice with $Na^+$ ion-exchange resin (1.5 g) for one hour. $^1$H-NMR ($CD_3OD$): $\delta 0.8$ (t, 3H, terminal methyl), 1.1 (t, 3H, $\underline{CH_3}CH_2O$), 1.2–1.4 [m, 28H, $(\underline{CH_2})_{14}$], 1.55 (m, 2H, $NHCOCH_2\underline{CH_2}$), 1.8 (s, 3H, Thymidine $\underline{CH_3}$), 2.2 (t, 2H, $NHCO\underline{CH_2}$), 2.2–2.5 (m, 2H, Thymidine 2' $\underline{CH_2}$), 3.3–3.8 [m, 16H, $CH_3\underline{CH_2}OCHCH_2NHCO$, $\underline{CH_2}N(CH_3)_3$) 3.9–4.2 (m, 5H, $\underline{CH_2}OPO$, Thymidine 4' CH, and 5' $\underline{CH_2}$]4.6 (m, 1H, Thymidine 3' $\underline{CH}$), 6.25 (m, 1H, Thymidine 1' CH), 7.8 (m, 2H, Thymidine C6 proton, NH). FAB Mass Spectrum (MH+ 2Na)$^+$; Theoretical 839. 3461, Observed 839.3463, 0.2 ppm.

EXAMPLE 22

3'-Azido-3'-deoxythymidine-5'-diphosphate-D,L- 3-hexadecyloxy-2-ethoxypropane (compound A'). This compound is prepared in essentially the same manner the compounds described above, except that 3-hexadecyloxy- 2-ethoxypropyl phosphatidic acid is used as the starting material.

EXAMPLE 23

Anti-HIV1 Activity of Lipid-Nucleoside Conjugates. CEM-SS cells were seeded (50,000 cells/ml RPMI-1640 growth medium) as a monolayer in 96-well dishes, innoculated with 50 to 100 plaque forming units of HIV-1 and overlaid with serial dilutions of lipid-nucleoside conjugate in RPHI-1640 growth medium. Plaques were counted after five days incubation at 37° C. to determine the 50% inhibitory concentration.

To determine the $IC_{50}$ for cell growth, cells in suspension culture (10,000 cells/ml RPHI-1640 growth medium) were incubated with serial dilutions compound at 37° C. for 48 hours and then pulsed labelled with 1 microCi of $^3$H-Tdr (SA=20 Ci/mmole) for 8 hours at 37° C. to measure DNA synthesis. Data are given in Table 4 below.

TABLE 4

EFFECT OF LIPID-NUCLEOSIDE CONJUGATES ON HIV-1 PLAQUE FORMATION

| Drug | HIV-1 Plaque Formation | CEM-SS Cell Growth | D.S.[b] |
|---|---|---|---|
| AZT | 0.004 | 5.1 | 1281 |
| AA | 0.004 | 13.5 | 3375 |
| BB | 0.04 | 13.7 | 342 |
| H | 0.011 | 6.6 | 600 |
| A' | 1.27 | >100 | >78.7 |

$IC_{50}$ (Micromolar)[a]

[a]Concentration required to inhibit 50% of either plaque formation or CEM-SS cell growth.
[b]Differential selectivity (D.S.) equals the average $IC_{50}$ for CEM-SS cell growth divided by the average $IC_{50}$ for HIV-1 plaque formation.

The foregoing examples are illustrative of the present invention, and are not to be construed as limiting thereof. For example, those skilled in the art will appreciate that minor changes can be made in the compounds disclosed herein which will not significantly adversely affect the activity and usefulness thereof. Accordingly, the invention is defined by the following claims, with equivalents of the claims to be included therein.

That which is claimed is:

1. A lipid-nucleoside conjugate or a salt thereof having the formula:

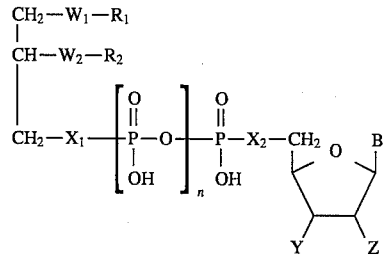

wherein:

R$_1$ is C15–C20 saturated or unsaturated alkyl containing not more than three double bonds;

R$_2$ is H or C1–C3 saturated alkyl;

W$_1$ is NHC(=O) or NH;

W$_2$ is S, O, NHC(=O), NH or a covalent bond;

n is zero or one;

X$_1$ and X$_2$ are each independently oxygen or a covalent bond, subject to the proviso that when n is zero, then at least either X$_1$ or X$_2$ is oxygen;

B is selected from the group consisting of adenine, thymine, cytosine, guanine, hypoxanthine, and uracil; and Y is H, F, or N$_3$; Z is H or F; or Y and Z together are a covalent bond.

2. A lipid-nucleoside conjugate according to claim 1, wherein R$_1$ is C16–C18 linear alkyl containing not more than one double bond.

3. A lipid-nucleoside conjugate according to claim 1, wherein Y is H or N$_3$; Z is H or F; or Y and Z together are a covalent bond.

4. A lipid-nucleoside conjugate according to claim 1, wherein Y is N$_3$, Z is H, and B is thymine.

5. A lipid-nucleoside conjugate according to claim 1, wherein n is 1, X$_1$ is oxygen and X$_2$ is oxygen.

6. A lipid-nucleoside conjugate according to claim 1, wherein n is zero, X$_1$ is oxygen and X$_2$ is oxygen.

7. A lipid-nucleoside conjugate according to claim 1, wherein n is zero, $X_1$ is a covalent bond and $X_2$ is oxygen.

8. A lipid-nucleoside conjugate according to claim 1, wherein n is zero, $X_1$ is oxygen and $X_2$ is covalent bond.

9. A lipid-nucleoside conjugate according to claim 1, which is 2,',3'-dideoxyinosine- 5'-monophosphate-D,L-3-octadecanamido-2-ethoxypropane.

10. A lipid-nucleoside conjugate according to claim 1, which is 3'-azido- 3'-deoxythymidine-5'-diphosphate-D,L-3-octadecanamido-2-ethoxypropane.

11. A lipid-nucleoside conjugate or a salt thereof having the formula:

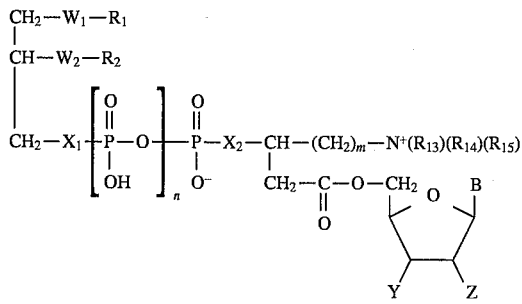

wherein:

$R_1$ is C10–C20 saturated or unsaturated alkyl containing not more than three double bonds;

$R_2$ is H or C1–C3 alkyl;

$W_1$ is S, O, NH or NHC(=O);

$W_2$ is S, O, NHC(=O), NH or a covalent bond;

n is zero or one;

$X_1$ and $X_2$ are each independently oxygen or a covalent bond, subject to the proviso that when n is zero, then at least either $X_1$ or $X_2$ is oxygen; m is 1 to 3;

B is selected from the group consisting of adenine, thymine, cytosine, guanine, hypoxanthine, and uracil;

Y is H, F, or $N_3$; Z is H or F; or Y and Z together are a covalent bond; and $R_{13}$, $R_{14}$, and $R_{15}$ are each independently either hydrogen or methyl.

12. A lipid-nucleoside conjugate according to claim 11, wherein X is NHC(=O).

13. A lipid-nucleoside conjugate according to claim 11, wherein $R_1$ is C16–C18 linear alkyl containing not more than one double bond.

14. A lipid-nucleoside conjugate according to claim 11, wherein n is 1.

15. A lipid-nucleoside conjugate according to claim 11, wherein $R_{13}$, $R_{14}$, and $R_{15}$ are methyl.

16. A lipid-nucleoside conjugate according to claim 11, wherein Y is H or $N_3$; Z is H; or Y and Z together are a covalent bond.

17. A lipid-nucleoside conjugate according to claim 11, wherein Y is H or $N_3$ and Z is H.

18. A lipid-nucleoside conjugate according to claim 11, comprising 3'-azido- 3'-deoxythymidine- 5'-butyrate-γ-N,N,N-trimethyl-ammonium-β-(1-phospho-2-ethoxy-3-hexadecanamidopropane).

19. A lipid-nucleoside conjugate according to claim 11, comprising 3'-azido-3'-deoxythymidine- 5'-butyrate-γ-N,N,N-trimethyl-ammonium-β-(1-phospho-2-ethoxy-3-octadecanamidopropane).

20. A lipid-nucleoside conjugate or a salt thereof having the formula:

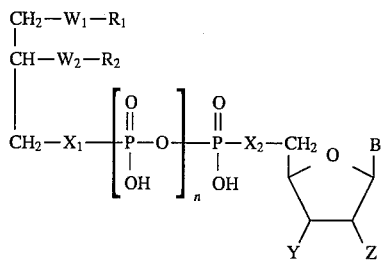

wherein:

$R_1$ is C10–C20 saturated or unsaturated alkyl containing not more than three double bonds;

$R_2$ is H or C1–C20 saturated alkyl;

$W_1$ is NHC(=O);

$W_2$ is O;

n is zero or one;

$X_1$ and $X_2$ are each independently oxygen or a covalent bond, subject to the proviso that when n is zero, then at least either $X_1$ or $X_2$ is oxygen;

B is selected from the group consisting of adenine, thymine, cytosine, guanine, hypoxanthine, and uracil; and Y is H, F, or $N_3$; Z is H or F; or Y and Z together are a covalent bond.

21. A lipid-nuclcoside conjugate according to claim 20 wherein n is 0, $X_1$ and $X_2$ are independently oxygen, B is thymine, Y is $N_3$ and Z is hydrogen.

* * * * *

UNITED STATES PATENT AND TRADEMARK OFFICE
CERTIFICATE OF CORRECTION

PATENT NO. : 5,512,671

DATED : April 30, 1996

INVENTOR(S) : Claude Piantadosi et al.

It is certified that error appears in the above-identified patent and that said Letters Patent is hereby corrected as shown below:

Cover page, in the Abstract, first line, delete "nucleoli" and insert therefor --nucleoside--.

Column 19, line 42, delete "X" and insert therefor --$W_1$--.

Column 20, line 39, delete "adeninc," and insert therefor --adenine,--.

Column 20, line 45, delete "lipid-nuclcoside" and insert therefor --lipid-nucleoside--.

Signed and Sealed this

Fourth Day of March, 1997

Attest:

BRUCE LEHMAN

*Attesting Officer*    *Commissioner of Patents and Trademarks*